Figure 1:
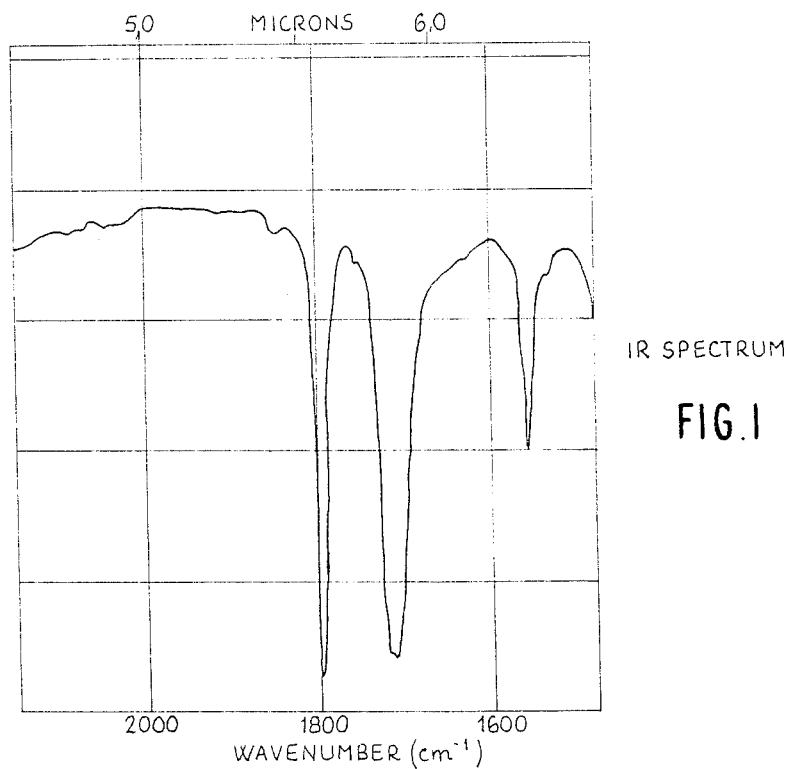

United States Patent [19]

Fedeli et al.

[11] Patent Number: 4,871,769
[45] Date of Patent: Oct. 3, 1989

[54] 2-TRICHLOROACETOXY-3,4,5,6-TETRA-CHLOROBENZOIC ACID AND COMPOSITIONS CONTAINING SAME FOR TREATING BENIGN MAMMALIAN NEOFORMATIONS

[75] Inventors: Gianfranco Fedeli, Milan; Giuseppe Diamantini, Fano; Wiktor Djaczenko; Maria Strumillo, both of Rome, all of Italy

[73] Assignees: Wiktor Djaczenko; Maria Strumillo, both of Rome, Italy

[21] Appl. No.: 11,468

[22] Filed: Feb. 5, 1987

Related U.S. Application Data

[63] Continuation-in-part of Ser. No. 815,092, Dec. 9, 1985, abandoned.

[30] Foreign Application Priority Data

Apr. 16, 1984 [IT] Italy .................. 48046 A/84

[51] Int. Cl.⁴ .................. A61K 31/22; C07C 69/63
[52] U.S. Cl. .................. 514/550; 560/226; 560/229
[58] Field of Search ............ 560/143, 145, 226, 227, 560/229; 514/547, 159, 163, 165, 548, 550; 562/474

[56] References Cited

U.S. PATENT DOCUMENTS

| | | | |
|---|---|---|---|
| 1,974,689 | 9/1934 | Pfaff and Erlenbach | 514/159 |
| 3,355,387 | 11/1967 | Hinkel, Jr. | 514/159 |
| 3,928,587 | 12/1975 | Sawyer | 514/159 |
| 3,995,034 | 11/1976 | Strobel | 514/159 |
| 4,588,590 | 5/1986 | Bernstein | 514/159 |

Primary Examiner—Donald B. Moyer
Assistant Examiner—Julie K. Parker
Attorney, Agent, or Firm—Beveridge, DeGrandi & Weilacher

[57] ABSTRACT

Tetrachlorobenzoic acid derivative having the formula:

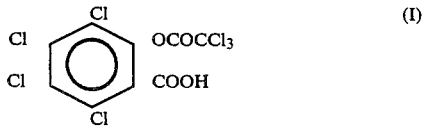

(2-trichloroacetoxy-3,4,5,6-tetrachlorobenzoic acid), chemotherapeutically active against cutaneous and subcutaneous benign neoformations, process for its preparations and compositions containing the same.

10 Claims, 3 Drawing Sheets

IR SPECTRUM (2-TRICHLOROACETOXY-3,4,5,6-TETRACHLOROBENZOIC ACID)

UV SPECTRUM

2-TRICHLOROACETOXY-3,4,5,6-TETRACHLOROBENZOIC ACID
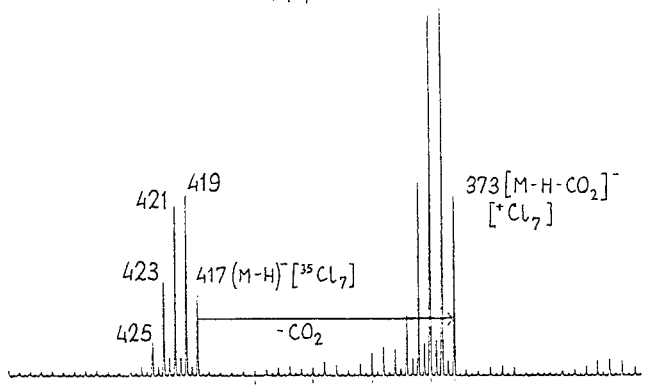
MASS SPECTRUM
FIG. 3
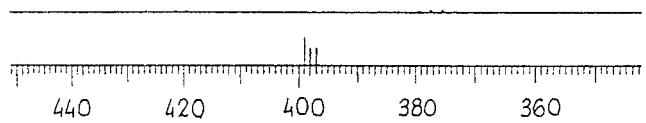
2-TRICHLOROACETOXY-3,4,5,6-TETRACHLOROBENZOIC ACID
FIG. 4
$C^{13}$-NMR
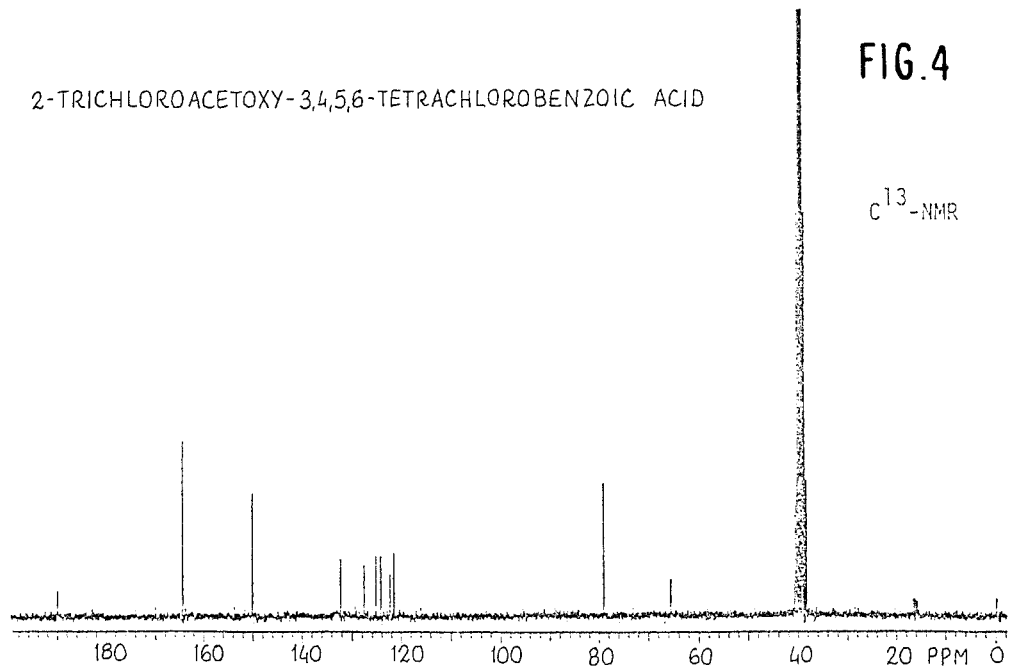

2-TRICHLOROACETOXY-3,4,5,6-TETRACHLOROBENZOIC ACID AND COMPOSITIONS CONTAINING SAME FOR TREATING BENIGN MAMMALIAN NEOFORMATIONS

This application is a contination-in-part of Ser. No. 06/815,092 filed Dec. 9, 1985, now abandoned.

DISCLOSURE OF THE INVENTION

1. Technical Field

This invention relates to 2-trichloroacetoxy-3,4,5,6-tetrachlorobenzoic acid, chemotherapeutically active against cutaneous or subcutaneous benigne neoformations, a process of its preparation and the compositions containing the same. More particularly, the invention is dealing with the use of 2-tetrachloroacetoxy-3,4,5,6-tetrachlorobenzoic acid in the manufacture of preparations having a pharmacological activity against cutaneous diseases, mainly those having an infective origin.

2. Background Art

As it is well known, "Principles of Surgery", Seymur I. Schwartz, Editor in Chief, G. T. Shires, E. H. Storer, F. C. Spencer, Mc Graw Hill 1979, New York, Principles of Internal Medicine, Harrison's G. W. Thorn, R. D. Adam, E. Braunwald, K. J. Isselbacher, R. G. Petersdorf 1977, Mc Graw-Hill, New York,) a therapy to resolve without collateral effects, the cutaneous lesions which are characteristic of the clinically benign neoformations treated with the product according to the invention, has not yet been found up to date.

These inconveniences are particularly significant in some cases, cited hereinbelow, as for inst. the different types of warts, the *Condyloma acuminatum* and the *Molluscum contagiosum*.

As it is known, warts are an infective disease of the skin and the adjacent mucoses attributable to a DNA virus having a diameter of 45 nm. This virus taken out of cutaneous lesions in patients suffering from warts, has induced the same lesions when inoculated in volunteers. The incubation time is 1-20 months, on the average 4 months. The virus invades the cell nucleus area, as it appears from the electronic microscopy images. Recently, the virus has been isolated from cell cultures in vitro. The cutaneous lesions induced by the warts' virus consists of an abnormal proliferation of the epithelial cells of epidermis.

These are single lesions or they can be spread in many body areas; they are characterized by a typical colour of the skin. Even if the warts' virus appears to be always the same, morphological appearance of the lesions changes greatly depending on the type of the reactions of the skin affected by the disease.

The main types of warts which can be treated by the composition according to the invention are the following ones:

(a) *Verruca vulgaris:*

It appears on the hands, under the nails or in the adjacent areas. The lesions have a rough surface and sometimes they look like corneous papulas. The diameter is in the rage from 1 mm to 2 cm. The "clusters"-forming warts can also be met making contiguous areas. Sometimes warts have asymptomatic clinical course. The first lesions have a strong attitude to spread.

(b) *Verruca plantaris:*

It appears in the pressure points of the sole. Symptomatology is very painful, lesions of corneus consistency are flat, hard and spotted. They can be single or "clusters"-forming lesions. The main body of the warts is under the skin cutaneous layer and therefore lesions are so painful. The plantar wart of conical shape cuts like a wedge the undercutaneous tissues, being this shape likely due to deambulation mechanics.

(c) *Verruca plana:*

It is a smooth, circular or polyogonal lesion, with normal cutaneous colour, in relief with respect to the cutaneous surface. The diameter of this lesion is usually in the range from 1 up to 5 mm. They can cover large cutaneous areas: sometimes it is possible to count several hundreds in only one individual. The preferred sites are face, back, neck, thorax, hands, thighs. Mucosas rarely suffer from warts.

(d) *Verruca filiformis:*

It may be noted in the adult males, usually in the bearded portion of the face. The lesions are corneous, fingershaped, sometimes they are very long.

(e) *Condyloma acuminatum:*

Lesions are in the muco-cutaneous areas of the skin junctions of the genital and perianal areas. Most rarely condyloma appear in the nipple area, at periphery of the mouth, in the inguinal axillary foldy and between the toes. Said lesions are pinky-red, wet and soft, tender. They can be pedunculated and lengthened. "Clusters" of said lesions look like a cauliflower. Ulcerations of said surfaces as well as bad smell particularly in some areas are frequent. As a fact, individuals of any age, but in particular women in pregnancy can suffer from said kind of wart.

Molluscum contagiosum

It is an infective disease of the skin and mucosas due to a virus which is the biggest one known up to date.

This disease is exclusive to humans, and very frequent in infancy.

The virus belongs to the pox virus group. No antigenic reaction occurs with other members of the pox virus.

The way it is spread is not known.

Epidemics of *molluscum contagiosum* have been noted, especially in the communities: barracks, colleges, orphanages, etc.

The disease is well known all over the world. Sometimes it looks like a venereal disease.

The incubation period ranges from 2 weeks up to two months. The individuals contain specific antibodies in their serum. The diameter of the lesions ranges from 1 up to 2 cm; the lesions, similar to papulas with an "umbelicus" in the center, are on relief, pale, pearly and whitish.

There are single papulas or "cluster"-forming papulas. The self-inoculation is frequent.

The face, palpebras, trunk, the anogenital areas are the preferred sites of the disease.

Concerning the present therapy of the abovementioned kind of warts, these are not free, as abovesaid, from clear inconveniences.

For instance, the *verruca vulgaris* is treated in different ways as by cryotherapy, use of caustic substances or cobalt-therapy.

The electro-extirpation in local anaesthesia is one of the most advanced surgical methods. It is to be noted that no one of said methods can definitely solve the problem of the *vulgaris verrucae*.

The inconveniences of these methods are large, post-therapeutic cicatrizations, serious pains during the different surgical operations and psychological trauma.

In particular, when cryotherapy is used, sometimes there are quite serious malformations as, for instance, the outward exposure of the bones of phalanges and moreover scars disfiguring the face, hands and large areas of the trunk skin.

However, the most serious problem consists of multiple relapses of the cutaneous infections after when many therapies have been adopted, in particular those occurring after the cryotherapy wherein the seeding of the warts (dissemination) goes beyond the areas originally affected. It is a current opinion to consider the methods used up to date for the *vulgaris verrucae* therapy as palliatives.

As to the chemiotherapy of the simple warts, it is to be noted the use of a large selection of products, from the local anaesthetics to the caustic substances.

Medicine has nothing to offer to the patients suffering from warts also in this case (see "Principles of Surgery—Schwartz, page 551). At present, surgical methods, as the extirpation of the Condyloma body in local anaesthesia, the chemiotherapy with topical application of podophillin (25%) prepared as a tincture in benzoin, are used. The main inconvenience of such a therapy is the presence of large and deep scalds of the adjacent intact skin when, as it frequently occurs, the compound comes out of the first lesion.

The cobalt-therapy can cause large cicatrizations. Sometimes serious complications, as, for instance, intestinal occlusion of the rectum due to unsuccessful attempts of multipla extirpation of the first condyloma, deformation of the perineum with incontinence, etc. have occurred. The silver nitrate used to treat the conyloma, can cause deep wounds having a slow recovery and in loco infections.

DISCLOSURE OF THE INVENTION

Therefore, it appears necessary to have at disposal a therapy suitable to face decisively the abovesaid cutaneous infections without the abovementioned inconveniences, often very serious.

This request is surprisingly satisfied according to the present invention by using a product not yet known, the 2-trichloroacetoxy-3,4,5,6-tetrachlorobenzoic acid.

It is further object of this invention to suggest advantageous procedures for its preparation and the preferred compositions containing said product.

It is therefore a specific object of the present invention a tetrachlorobenzoic acid derivative having the formula

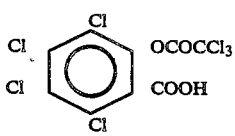

(2-trichlorocetoxy-3,4,5,6-tetrachlorobenzoic acid), chemotherapeutically active against cutaneous and subcutaneous benign neoformations. The process for the preparation of the compound of formula (I), according to the present invention starting from tetrachlorophthalic anhydride, provides for the following succesion of steps:

(a) treatment of the anhydride (II) with ammonia and immediate alkaline degradation of the amide (III) so formed (ref. V. Villinger, L. Blangey—BER 42, 3549-53, (1909);

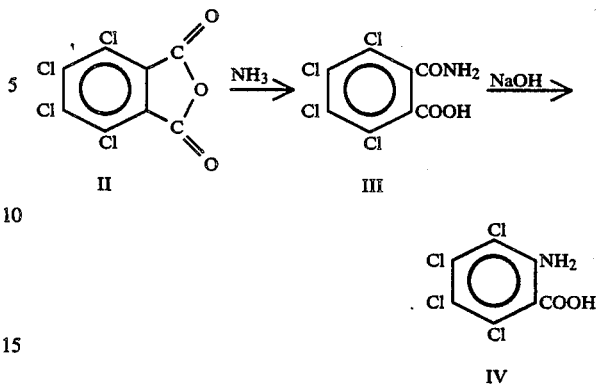

(b) diazotization of the corresponding anthranilic acid (IV) and successive hydrolysis to obtain 2-hydroxy-3,4,5,6-tetrachlorobenzoic acid (V) (ref. R. Howe, J. Chem. Soc., Org. 1966 (4), 478-480);

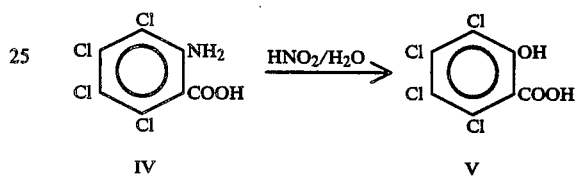

(c) esterification with a reactive derivative of trichloroacetic acid:

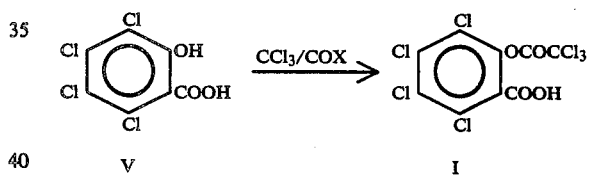

The compositions based on the active compound of formula (I) to be adopted according to the present invention consist in:

(a) oily or lipidic solutions (for instance, oil and/or lanolin) containing 1-25% of (I);

(b) ointment formulations made up of glycerol and starch containing as a mixture 1-12% and preferably 6% of (I);

(c) water solutions or physiologic solutions instantly prepared by addition for instance of triethanolamine for adjusting the pH value within a range from 5 to 8, and preferably for adjusting the pH value at 6.5.

As aforesaid, the invention suggests the 2-trichloroacetoxy-3,4,5,6-tetrachlorobenzoic acid for the therapy of cutaneous clinically benign neoformations, mainly those of infective origin.

It is to be noted that the compound of formula (I) is a medicine really active either for the non-traumatic healing of the lesion, or for the prevention of relapse and the scars arising after the surgical operation. Analogously it is suitable to revise the therapies adopted in this field in other centers and with other methods.

Practically, as the experiences based on the nephelometic technics demonstrate, the product according to the invention has the property of modifying the proteinic structures making a distinction between the normal and the pathological proteins.

A great range of conjugate proteins has been used in the research, allowing to state a quantitative relation between the product concentration and the entity of deviation of the proteinic structure from the main one. A 6% concentration appears to assure the highest specificity of the medicine, that is the possibility of a different action with respect to the normal and pathologic proteins.

Moreover, in the case of normal protein, reversible complexes are formed, while the proteins extracted from lesions like verrucae or *molluscum contagiosum*, seem to be in an irreversible state, after a contact with the product according to the invention.

The product according to the invention has proven to be active also in the following cases: (1) Cheloid; (2) Capillary Hemangioma; (3) Cavernous Hemangioma; (4) Glomus-tumor.

The clinical experiments in more than 1000 cases have demonstrated that compositions according to the present invention containing, in an aqueous solution, 6% of the compound of formula (I) and 1,2% of NaCl, local anaesthetics or not, is active by 100% in the therapy of all kinds of warts. There is however a different time interval to gain recovery. As a fact the "vulgaris" warts and the sharp condiloma need to be treated with a different number of applications of the product.

Moreover, the closeness of keratin or of the connective tissue in the warts can also influence the number of the applications. The product is for external use only.

In the great majority, the composition is applied without local anaesthetics.

When the warts are not treated, compact or deeply anchored to the subcutaneous tissue, 2% lidocaine is added in an amount of 0,1 ml. To make the medicine penetration easier in the case of very compact warts, small canals are produced on the tissue of wart in an attempt to soak up the tissue by the quantity of therapeutic liquid. It occurs without pain. The penetration of the active substance on the intact tissue is without pain, too.

The obtaining of the therapeutical canal in the subcutaneous tissue in case of deep roots, causes slight smart for about 1 minute.

However, local anaesthetics can be used without any lack of therapeutical activity in sensitive patients. Contact with intact skin does not provoke any alteration, on the contrary, the liquid appears to help the physiological recovery of the skin damaged by the first application of anti-warts therapy or by other trauma of all kind.

The whitish colour assumed by the intact skin when contacted by the medicine, disappears after a few days making the skin soft, smooth, natural coloured and exactly wet. The outcome of this therapy of the warts can be described as follows: during the therapy the superficial layers of the wart flake off, and the layer adjacent to the skin is left untreated.

For a few days the normal growth of the intact skin physiologically eliminates the last portions of the wart so that, after the underneath intact skin has been eliminated, the wart assumes the same features of the surrounding skin, without scars and other alterations. With the passing of time, it is not possible anymore to recognize the main seat of the wart.

A canal contact of the mucosa and of the eyes with the therapeutical liquid can cause an itching for at least 5 minutes, due to osmotic effects. Employing the therapeutical concentration, lesions of the mucosa or of the eyes have not been observed in any case. The product according to the invention, in 6% concentration, is highly bactericidal, coagulative and antiseptic, therefore the large contrast with the areas affected by warts or other kind of cutaneous lesions does not produce hemorrhage or contagious infection.

When the medicine is employed with such concentrations, it is antiviral and this fact probably explains the lack of relapses after having eliminated the warts also when applications following other therapeutical means are employed.

On the edges of the treated cutaneous lesions hyperemic areas are noted, probably due to immunostimulating action of the compound according to the invention.

The average of applications to obtain a complete resolution of the pathologic problem is 3 for *verrucae vulgaris*, even if spread on large areas of the body. Very compact warts need about 6 applications; Flat warts disappear also after only one application, so as the sharp condyloma and the molluscum contagiosum.

Exceptional results can be observed for gigantic sharp condyloma where an exactly dosed sole application can get rid of 90% of the lesion. The amount of the medicine for getting rid of a wart having mean dimension is about 0,5 ml.

In case of gigantic sharp condyloma, it is possible to use up to 10 ml of the liquid.

Toxicity 2-trichloroacetoxy-3,4,5,6-tetrachlorobenzoic acid at a therapeutical or higher concentration is not absorbed by the subcutaneous tissues and so there is no problem of internal toxicity. The lowest concentrations can be absorbed, but, as it has been demonstrated by the experiments on the laboratory animals the penetration is not deep and no alteration of the internal organs in the mouse has been evidenced up to date by means of electron microscope after transcutaneous administration at low concentration. No pathologic affect has been noted in the skin areas which were original seats of a wart previously treated with traumatic surgical operations inducing deep scars, and then by the application of the product of this invention. The low concentration of about 0,1% used in the application to tissues in vitro, do not induce any alteration on said tissues.

Higher concentrations cause damages to the cultures for osmotic reasons. People working the synthesis of the product for several years, and so exposed to the directed action of the product according to the invention, or to the contact with the hand skin at high concentration (35%), or to inhalation of the powders of this substance during the packaging, or by breathing of the vapours of the product.

Some examples of preparation of 2-trichloroacetoxy-3,4,5,6-tetrachlorobenzoic acid according to the schematic procedure outlined above are illustrated in the following just for indication purposes.

EXAMPLE 1

Figure 2:
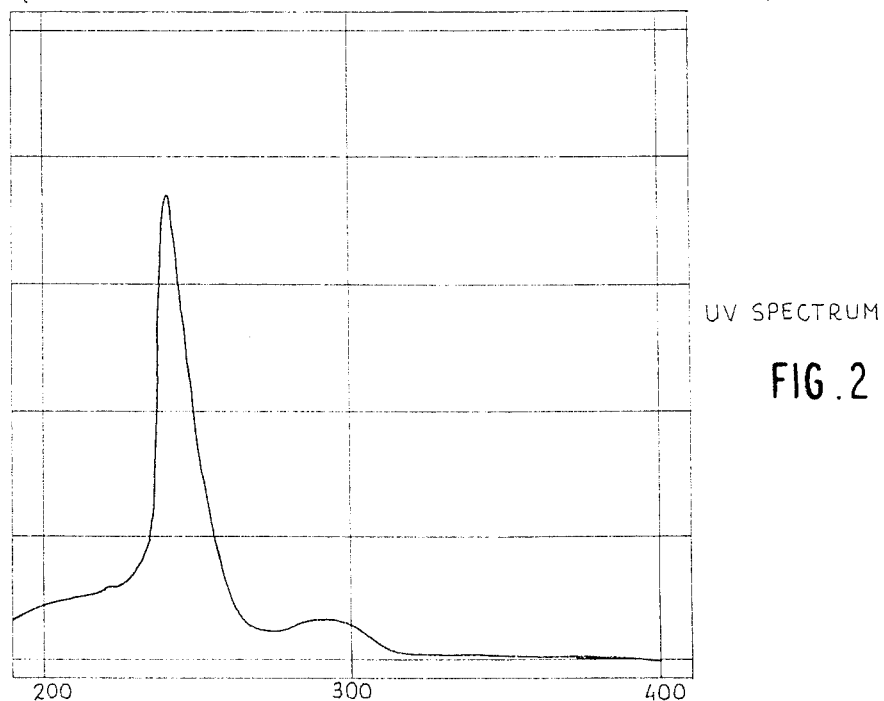

2 g of 2-hydroxy-3,4,5,6-tetrachlorobenzoic acid (IV-7.25 mM) was dissolved in 36 ml of 3N sodium hydroxide. 110 g of crushed ice and 26 ml of trichloroacetic anhydride was added to the resulting solution. The reaction flask was stoppered and shaken vigorously for some minutes. The white precipitate so obtained was extracted with dichloromethane. Such extract was then washed with water, dried on sodium sulfate and evaporated under reduced pressure. The residue obtained (2.9 g) was crystallized from n-hexane. 1.9 g was obtained of the desired product having the following properties:

analytical composition:
C=25.8% (theoretical value 25.7%)
H=0.3% (Theor. val. 0.24%)
N=absent
melting point (on a silicone oil bath apparatus)=141.5°-142.5° C.
IR spectrum: main peaks
strong peak at 1800 cm$^{-1}$ of the C=O group of the ether;
wide and strong peak at 1720-1730 cm$^{-1}$ of the C=O of the acid group (see the attached spectrum);
UV spectrum (in chloroform at 40 mcg/ml):
$\lambda_{max}$ at 240 nm (main)
$\lambda_{max}$ at 292 nm
$\lambda_{min}$ at 273 nm FIGS. 1 and 2, respectively, show IR and UV spectra.

EXAMPLE 2

2 g of 2-hydroxy-3,4,5,6-tetrachlorobenzoic acid (IV-7.25 mM) was dissolved in 200 ml of dioxane. 1.2 ml of anhydrous triethylamine and 1 ml of trichloroacetic acid chloride was added to the solution as obtained. The mixture was stirred at room temperature for 30 minutes keeping the same free from damp, and then said mixture was diluted with 1 l of dichloromethane. The organic solution so obtained was first washed with acid water and then with water, dried on sodium sulfate and evaporated under reduced pressure. The residue so obtained (3.6 g) was crystallized from n-hexane. 1.9 g was obtained of the desired product having the following properties:

analytical composition:
C=25.54% (theoretical value 25.7%)
H=0.21% (theor. val. 0.24%)
N=absent
melting point=141°-142° C.
IR and UV spectra as in the example shown above;
mass spectrophotometry:
molecular ion M, put into evidence with FAB only, having masses of 417 (FAB$^-$) and 419 (FAB$^+$)
presence of a cluster corresponding to that simulated on the computer for 7 Cl atoms, respecting the natural abundance ratios of the isotopes
the carboxylic acid structure put into evidence by the presence of a second cluster shifted by 44 mass units FIG. 3 shows details of mass spectrum.
NMR spectrum The C$^{13}$-NMR spectrum (equipment Varian XL 200) obtained at the frequency of 50 MHz, in dimethyl-sulfoxide solution showed:

| CHARACTERISTIC SIGNALS | ASSIGNABLE FUNCTIONAL GROUPS |
|---|---|
| delta ppm 79 (s) | —CCl$_3$ |
| delta ppm 121,5 (s) | Cl |
| delta ppm 122,3 (s) | C3 or C5 |
| delta ppm 124,1 (s) | C3 or C5 |
| delta ppm 125,2 (s) | C3 or C5 |
| delta ppm 127,6 (s) | C6 |
| delta ppm 132,3 (s) | C4 |
| delta ppm 150,2 (s) | C2-O— |
| delta ppm 164,4 (s) | 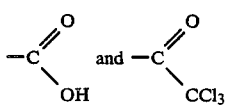 |

FIG. 4 shows C$^{13}$-NMR spectrum.

The present invention has been disclosed with particular reference to some specific embodiments but it is to be understood that modifications and changes can be introduced in the above disclosure without departing from its true spirit and scope.

We claim:

1. The compound 2-trichloroacetoxy-3,4,5,6-tetrachlorobenzoic acid.

2. A composition for treating bengin mammalian neoformations which comprises from 1 to 25% of the compound as claimed in claim 1 in an oily or a lipidic solution.

3. A composition for treating benign mammalian neoformations which comprises glycerol and starch or any other similar carrier compound, as a mixture with an amount of 1-12% of the compound as claimed in claim 1.

4. A composition for treating benign mammalian neoformations which comprises from 1 to 12% of the compound as claimed in claim 1 as a water or a physiological solution, the pH value being adjusted to between 5 and 8.

5. A composition according to claim 4 wherein triethanolamine has been employed for adjusting its pH value.

6. A composition as claimed in claim 3 in which the amount of the compound is 6%.

7. A composition as claimed in claim 4 in which the amount of the compound is 6%.

8. A composition as claimed in claim 4 in which the pH value is 6.5.

9. A composition as claimed in claim 5 in which the pH value is 6.5.

10. A composition as claimed in claim 7 in which the pH value is 6.5.

* * * * *